United States Patent [19]

Braid

[11] 4,225,448

[45] Sep. 30, 1980

[54] COPPER THIOBIS(ALKYLPHENOLS) AND ANTIOXIDANT COMPOSITIONS THEREOF

[75] Inventor: Milton Braid, Westmont, N.J.

[73] Assignee: Mobil Oil Corporation, New York, N.Y.

[21] Appl. No.: 931,572

[22] Filed: Aug. 7, 1978

[51] Int. Cl.³ .............................................. C10M 1/54
[52] U.S. Cl. ..................... 252/42.7; 44/68; 252/400 R; 260/45.75 C; 260/438.1
[58] Field of Search ...................... 260/438.1, 45.75 C; 252/42.7, 400 R; 44/68

[56] References Cited

U.S. PATENT DOCUMENTS

| | | | |
|---|---|---|---|
| 2,402,448 | 6/1946 | Richards | 252/42.7 |
| 2,409,303 | 10/1946 | Morris et al. | 252/42.7 |
| 2,449,026 | 9/1948 | Van Gilder | 260/438.1 X |
| 2,459,063 | 1/1949 | Cook et al. | 260/438.1 X |
| 2,515,129 | 7/1950 | Lieber et al. | 260/438.1 X |
| 2,971,940 | 2/1961 | Fuchsman et al. | 260/439 R X |
| 2,971,941 | 2/1961 | Fuchsman et al. | 260/439 R X |
| 2,971,968 | 2/1961 | Nicholson et al. | 260/439 R |
| 3,200,135 | 8/1965 | Cutler | 260/438.1 X |
| 3,390,160 | 6/1968 | Heller et al. | 260/438.1 X |
| 4,090,970 | 5/1978 | Braid | 252/42.7 |

Primary Examiner—Helen M. S. Sneed
Attorney, Agent, or Firm—Charles A. Huggett; Raymond W. Barclay; Howard M. Flournoy

[57] ABSTRACT

Novel copper thiobis(alkylphenol-phenolate) complexes are effective antioxidant additives for various organic media such as oils of lubricating viscosity and plastics. Additionally these novel copper organo-sulfur compounds are highly useful as energy quenchers and antisludging agents in a variety of organic substrates.

7 Claims, No Drawings

COPPER THIOBIS(ALKYLPHENOLS) AND ANTIOXIDANT COMPOSITIONS THEREOF

BACKGROUND OF THE INVENTION

1. Field of the Invention

This invention relates to novel copper thiobis(alkylphenol-phenolates) and to various organic compositions, such as lubricants and plastics, normally subject to oxidative degradation, containing a minor amount of said copper complexes, sufficient to impart antioxidant characteristics thereto. Additionally, this invention relates to organic compositions comprising said organic media and a minor amount of the copper compound in accordance with this disclosure thereby providing effective energy quenching stabilization and antisludging properties thereto.

In a more particular aspect this invention is directed to the above referred to novel copper phenolates and lubricant compositions containing them, which lubricant compositions include oils of lubricating viscosity, hydrocracked lubricating oils, hydraulic oils, automotive oils, gear oils, transmission fluids, waxes, greases and other forms which may be derived from mineral oils, or fractions thereof or are synthetic, of lubricants normally requiring the presence of stabilizing agents against oxidative degradation.

Also included within the scope of this invention are synergistic combinations comprising the aforesaid copper phenolates and hindered phenols and/or arylamines.

2. Description of the Prior Art

In general, the production of lubricant compositions, for example, lubricating oils produced by hydrocracking, affords a relatively high viscosity index and permits the use of certain stocks that would be unsuitable for other processes. However, hydrocracked lubricating oils tend toward poor stability against ultraviolet light degradation, rapidly forming suspended and/or precipitated insoluble material on exposure to ultraviolet light, such as sunlight, or other sources of actinic radiation. Compounds capable of absorbing ultraviolet light, for example, hydroxybenzophenones, and hydroxyphenyl benzotriazoles, have afforded some improvement in the light stability of hydrocracked oils. Conventional antioxidants have also provided some benefit. However, the copper complexes of this invention are believed to be novel.

In the literature, Heskins and Guillet in "Mechanism of Ultraviolet Stabilization of Polymers," Macromolecules 1, 97 (1968) first proposed the energy transfer mechanism of ultraviolet protection. Commercially available ultraviolet stabilizers are also listed by class and function and identified as to structure in the Kirk-Othmer Encyclopedia in "Encyclopedia of Chemical Technology," Second Edition, Vol. 21, pp. 115–122. Uri in "Thermal and Photochemical Oxidation of Polymers and Its Prevention," Chemistry and Industry, Mar. 1, 1975, pp. 199–203, cites conventional antioxidant effects (hydroperoxide decomposition and free radical capture) of bis(stilbenedithiolato)nickel and its ultraviolet inhibiting properties. In British Pat. No. 1,263,910 (1972), there is disclosed bis(stilbenedithiolato)nickel as an antioxidant for plastic materials. The compounds being useful in lube oils and functional fluids. Further, U.S. Pat. Nos. 2,703,786, 2,716,090 and 3,210,277 disclose the use of polyvalent metal (e.g. Ni) salts of alkyl phenol sulfides as oxidation inhibitors and plasticizing agents. Various polyvalent metal (e.g. nickel) compounds are disclosed in the patent literature, for example, U.S. Pat. No. 3,630,897 discloses metal salts (e.g., nickel, iron, zinc) of substituted dithiocarbamic acids and U.S. Pat. No. 3,252,910 discloses compounds such as nickel N,N-substituted dithiooxamides. U.S. Pat. No. 2,971,940 and 2,971,941 disclose nickel phenol-phenolate complexes as being useful in stabilizing polyethylene and polypropylene.

None of the foregoing disclosures, however, show organic, e.g., lubricant compositions containing the organosulfur-containing copper complexes described in accordance with this invention.

SUMMARY OF THE INVENTION

This application is predicated on the discoveries (1) of certain novel organo-sulfur-containing copper compounds and (2) that organic compositions of improved antioxidant characteristics, ultraviolet light and energy quenching stabilization and antisludging properties are provided when these novel organosulfur copper compounds are added thereto in minor effective amounts.

The organic sulfur-containing copper compounds in accordance with the present invention are directed to copper thiobis(alkylphenol-phenolates) having the following structures:

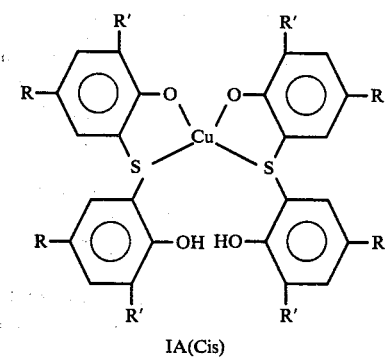

IA(Cis)

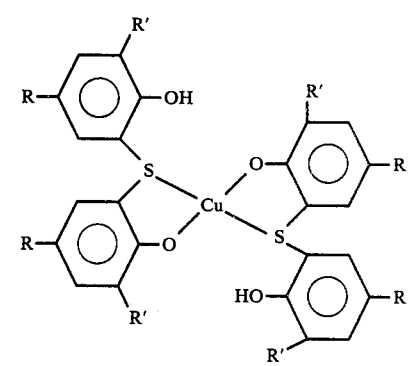

IB(Trans)

-continued

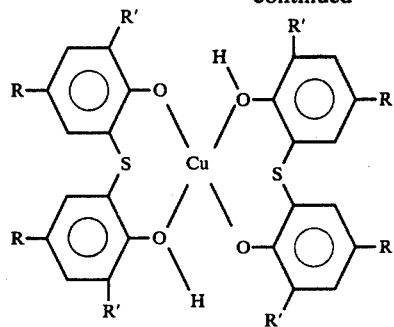

II

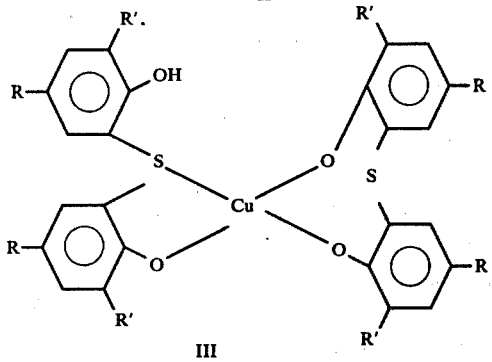

III in which R is either hydrogen or an alkyl group having from 1 to about 30 carbon atoms and, preferably 1-16 or 4-8 carbon atoms in any isomeric arrangement and R' is either hydrogen or an alkyl group having from 1-8 carbon atoms in any isomeric arrangement except that the carbon atom bonded (or attached) to the ring carbon atom is attached to no more than two other carbon atoms. Particularly preferred are alkyl groups wherein R is $C_8H_{17}$ and 1,1,3,3-tetramethylbutyl.

This application therefore is directed to compounds of copper prepared by a suitable reaction with thiobis (alkylphenol) under appropriate conditions of temperature, pressure and time wherein the desired product is formed.

The copper complexes of the thiobis(alkylphenols) nevertheless can be prepared in several ways. Reaction of the thiobis(alkylphenol) with a copper carboxylate for example, copper acetate in 2:1 molar ratio may be carried out in a nonreactive solvent such as xylene and the acetic acid may be removed as a binary azeotrope with xylene. The reaction temperature depends on the solvent used and is generally higher than the boiling point of the carboxylic acid liberated. Alternatively, a copper II salt such as copper II chloride or copper II nitrate may be reacted with alkali metal salts of a thiobis(alkylphenolate) for example potassium or sodium thiobis(alkylphenolate) in ethanol or propanol. The insoluble inorganic alkali metal salt formed is separated and the alcohol is then completely removed.

General reaction conditions: as noted previously temperature is dependent upon the solvent used and is often about 5°-25° C. below the solvent's BP during the azeotropic distillation process; atmospheric pressure or higher or lower, if desired, may be used; reaction duration will of course vary with temperature and pressure.

As hereinbefore indicated, the organic sulfur-containing copper complexes may be incorporated in various organic media which can include mineral oils of lubricating viscosity and also greases in which any of the oils mentioned herein may be employed as vehicles. In general, synthetic oils can also be effectively protected against oxidative and UV degradation or may also be employed in combination with mineral oils, or as grease vehicles. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxy phenyl) ether, and phenoxyphenylether.

The organosulfur-containing copper phenolates in accordance with this invention can be effectively employed in any amount which is sufficient for imparting to the organic medium, e.g., lubricant, the desired degree of protection against oxidative degradation. In many instances, the copper (II) complex is effectively employed in an amount from about 0.01 to about 5%, by weight, and preferably in an amount from about 0.1 to about 2%, by weight, of the organic composition.

As mentioned hereinabove the novel copper phenolate complexes of this invention function as effective antioxidant additives, or provide effective stabilization against ultraviolet degradation and also act as effective energy quencher stabilizers when incorporated into certain organic media. Therefore, this application is further particularly directed to compositions comprising a major amount of an organic medium normally susceptible to oxidative degradation and a minor amount effective to impart antioxidant characteristics thereto and/or to stabilize said composition against ultraviolet degradation and/or to impart energy quenching stabilization and/or antisludging properties thereto of an organo-sulfur containing copper thiobis phenolate complex.

The additive compounds disclosed herein form synergistic and improved mixtures when used in combination with arylamines and/or hindered phenols. Accordingly, this application is also directed to additive mixtures adapted to impart antioxidative characteristics to an organic medium normally susceptible to oxidative degradation consisting essentially of a copper organo-sulfur compound as described herein and an arylamine and/or a hindered phenol.

The arylamines used herein are preferably selected from the group consisting of the following: N-phenyl-1-naphthylamine; N-(4'-t-octylphenyl)-1-naphthylamine; 1,1'-thiobis (N-phenyl-2-naphthylamine); diphenylamine; dioctoxydiphenylamine; and phenothiazine. Especially preferred are phenyl naphthylamines such as N-phenyl-1-naphthylamine, N-(4-t-octylphenyl)-1-naphthylamine and N-phenyl-2-naphthylamine. However, it is understood that this is a non-limiting list and any arylamine appropriate in view of those disclosed above may be used.

Any suitable hindered phenolic compound may be used herein. Preferred are those selected from the following non-exhaustive list: 2,6-di-t-butyl-p-cresol; 4,4'-methylenebis-(2-6-di-t-butyl-m-cresol); 4,4'-butylidenebis(6-t-butyl-m-cresol) 4,4'-methylenebis-(2,6-di-t-butylphenol); 2,6-di-t-butylphenol, and 4,4'butylidinebis-(2,6-di-t-butylphenol) 2,4,6-tri-t-butyl-phenol. Especially preferred is 4,4'-methylenebis-(2,6-di-t-butylphenol).

Generally the weight ratio of the copper compound to arylamine and/or hindered phenol is from about 0.01–5.0 to 1.

DESCRIPTION OF SPECIFIC EMBODIMENTS 2,2'-thiobis-(4-t-octylphenol), representative of 2,2'-thiobis(alkylphenols) forms novel copper-containing complex by, for example, as previously mentioned herein above reaction with copper salts. The specific complexes synthesized with the specified thiobis(alkylphenol) have the same properties (2:1) of phenol to metal as previously disclosed nickel compounds but are different in structure.

EXAMPLE 1

Base substrate: hexadecane which simulates a typical mineral oil base.

EXAMPLE 2

Nickel 2,2'-thiobis-(4-t-octylphenol-phenolate): a commercially available prior art antioxidant/UV stabilizer prepared herein accordance with U.S. Pat. No. 2,971,941.

EXAMPLE 3

A mixture of 2,2'-thiobis-(4-t-octylphenol) (100 g.) and copper II acetate monohydrate (22.8 g.) in xylene (300 ml) was refluxed while stirring for about 1 hr. while all of the water and some acetic acid was removed as an azeotropic distillate. Heating and stirring were continued for an additional 4.5 hr. during which xylene and acetic acid were azeotropically distilled from the reaction mixture and fresh xylene was added concurrently to replace the distillate. At the end of this period acetic acid could no longer be detected in the distillate. Xylene solvent was removed from the reaction mixture by rotary evaporation. The dark brown semi-solid residue was extracted with cyclohexane. The insoluble solids (41.9 g.) were recrystallized from isooctane to afford the brown solid copper complex, m.p. 150°–155° C., for which the elemental analysis corresponded to a composition containing copper and 2,2'-thiobis(4-t-octylphenol) in the ratio of 1:2. Isomer A, i.e., Structure IA, II or III.

Analysis: Calc'd for $C_{56}H_{82}O_4S_2Cu$: C, 71.03; H, 8.73; S, 6.77; Cu, 6.71; Found: C, 70.13; H, 8.85; S, 6.31; Cu, 6.00

Remaining in the crystallizing solvent are mixtures of the remaining isomers, e.g., if IA is the cyrstalline product, then IB, II and/or III remain in the solvent and these are useful, as well.

EXAMPLE 4

The mixture of Example 3 was further treated as follows:

Evaporation of solvent from the cyclohexane extract left a brown solid residue which was treated with petroleum either, b.p. 30°–60° C. to separate a small amount of unreacted thiobis(alkylphenol). The mixture was filtered and the filtrate was stripped of the solvent to leave as a brown solid residue (54.6 g.), an isomeric copper complex of 2,2'-thiobis(4-t-octylphenol), m.p. 108°–112° C., with elemental analysis again corresponding to a ratio of 1:2. Isomer B, i.e., Structure IB, II, or III.

Analysis: Calc'd for $C_{56}H_{82}O_4S_2Cu$: C, 71.03; H, 8.73; S, 6.77; Cu, 6.71; Found: C, 70.84; H, 8.52; S, 6.54; Cu, 6.31.

The above prepared isomers of copper 2,2'-thiobis-(4-t-octylphenol-phenolate) were tested for their oxidation inhibiting characteristics in the modified Dornte Test and the Catalytic Oxidation Test; see data below.

Oxygen Absorption Test

Oxidations were conducted in an oxygen circulation apparatus of the type described by Dornte*, modified so the rate of oxygen absorption could be recorded automatically. The 30 g. sample was placed in a 28×260 mm tube and allowed to equilibrate thermally before the oxygen flow was begun. Oxygen was introduced to the sample at a rate of 5 liters per hour through a fritted glass disk 3 mm from the bottom of the tube. The inhibition period, $t_{1.0}$, was taken as the time required for the absorption of 1.0 mol oxygen per Kg of sample.
*R. W. Dornte, Ind. Engr. Chem., 28, 26 (1936).

Table 1 demonstrates the highly effective antioxidant properties of the copper phenolates embodied herein in mineral-oil base stock.

The organo-copper complexes of this invention were also tested in a *Catalytic Oxidation Test* for lubricants, using as the base medium a lubricant. The test lubricant composition is subjected to a stream of air which is bubbled through the composition at a rate of 5 liters per hour at 325° F. for 40 hours. Present in the composition are metals commonly used as materials of engine construction, namely:

(a) 15.6 sq. in. of sand-blasted iron wire,
(b) 0.78 sq. in. of polished copper wire,
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number ($\Delta NN$) and kinematic viscosity ($\Delta KV$) occasioned by the oxidation.

Compounds in accordance with this invention tested for their oxidative stabilizing properties in accordance with the above Catalytic Oxidative Test proved highly effective oxidation stabilizers and/or inhibitors. However, it should be noted that these compounds are equally useful in stabilizing plastics, e.g., polyolefins. The results of the test are reported in Table 2.

As will be noted from Table 2, the oxidation life of the base oil was markedly increased by the antioxidant effect imparted by the copper additives in accordance with the present invention.

TABLE 1
INHIBITION OF HEXADECANE ANTIOXIDATION AT 175° C.[1]

| Example | Additive | Conc. of Additive Mol/kg ($\times 10^3$) | Inhibition Period for Oxygen Absorption, Hr., $(t_{1.0})$[2] |
|---|---|---|---|
| 1 | None | — | 1.2; 1.1 |
| 2 | Nickel 2,2'-Thiobis-(4-t-octylphenol-phenolate) | 5 | 19.1 |
| 3 | Copper 2,2'-Thiobis-(4-t-octylphenol) Complex (Isomer A) | 5 | 22.1 |
| 4 | Copper 2,2'-Thiobis-(4-t-octylphenol) Complex (Isomer B) | 5 | 12.9 |

[1]Modified Dornte Test
[2]Time (hr.) required to absorb 1 mol. of oxygen/kg of oil

TABLE 2
Catalytic Oxidation Test 325° F., 40 Hr., Base Stock[1]

| Example | Additive | Conc., Wt. % |
|---|---|---|
| 1 | None | — |
| 2 |  | 2 |
|  |  | 1 |
|  |  | 0.5 |
| 2 | + 1% of MEB[2] | 1 |
|  | + 1% of MEB | 0.5 |
| 2 | + 0.5% of MEB[2] | 1 |
|  | + 0.5% of MEB | 0.5 |
| 2 | Cu(TBP)$_2$ + 0.5% of DDPA[3] | 1 |
|  |  | 0.5 |
| 2 | MEB[2] | 2 |
|  |  | 1 |
| 2 | DDPA[3] | 2 |
|  |  | 1 |

| Example | ΔNN | ΔKV % | Oxidized Oil Lead Loss, mg | Sludge |
|---|---|---|---|---|
| 1 | 17 | 334 | 66 | Heavy |
|  | 17.8 | 202 | 171.3 | Light |
| 2 | <0.1 | 28 | 0.3 | Heavy |
|  | 0.23 | 15 | 0.2 | Heavy |
|  | 1.58 | 15 | 0.6 | Heavy |
| 2 | 0.34 | 30 | 0.4 | Heavy |
|  | 1.10 | 18 | — | Heavy |
| 2 | 1.33 | 32 | — | Heavy |
|  | 2.22 | 33 | 0.1 | Heavy |
| 2 | 0.39 | 18 | 0.4 | Heavy |
|  | 1.07 | 16 | 0.2 | Heavy |
| MEB | 4.63 | 34 | — | Moderate |
|  | 5.23 | 47 | — | Heavy |
| DDPA | 1.34 | 18 | 0.3 | Light |
|  | 1.76 | 12 | 0.1 | Moderate |

[1]Base stock, a typical solvent refined lubricating oil
[2]4,4'-Methylenebis-(2,6-di-tert-butylphenol)
[3]Dioctxydiphenylamine

What is claimed is:

1. A composition comprising a major proportion of an organic medium normally susceptible to oxidative degradation and a minor amount sufficient to impart antioxidant properties thereto of a copper organo-sulfur-containing complex wherein said copper organo-sulfur-containing complex has the following general structures:

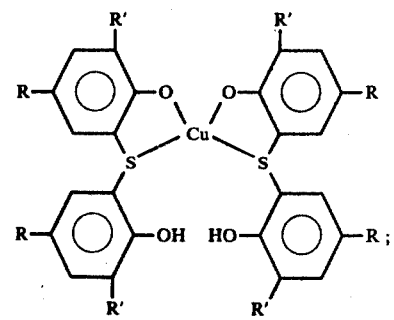

I

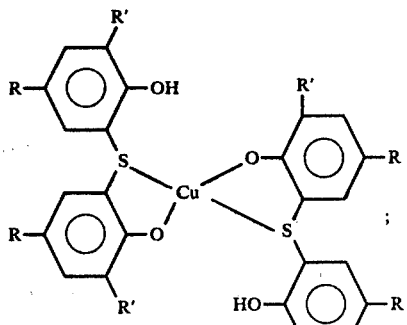

II

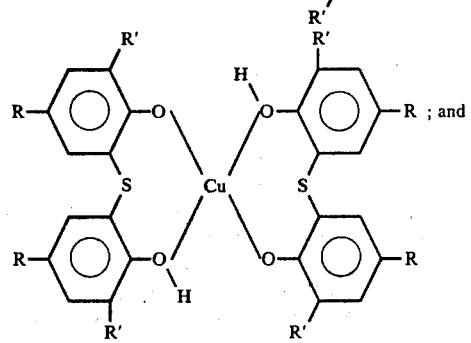

III ; and

-continued

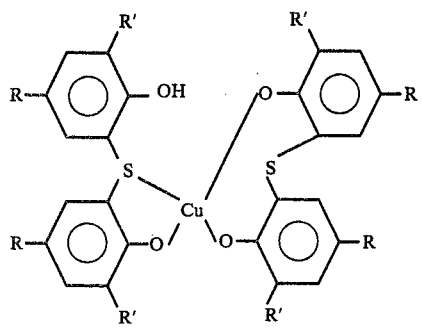

IV or mixtures thereof in which R is 1,1,3,3-tetramethylbutyl or a 4-t-octyl group and R' is either hydrogen or an alkyl group having from 1–8 carbon atoms in any isomeric arrangement except that the carbon atom bonded (or attached) to the ring carbon atom is attached to no more than two other carbon atoms.

2. The composition of claim 1 in which each R of said organo-sulfur complex is a 4-t-octyl group.

3. The composition of claim 1 in which each R of said organo-sulfur complex is a 1,1,3,3-tetramethylbutyl group.

4. The composition of claims 1 or 3 in which the organo-sulfur-containing complex is in accordance with structure I.

5. The composition of claims 1 or 3 in which the organo-sulfur containing complex is in accordance with structure II.

6. The composition of claims 1 or 3 in which the organo-sulfur containing complex is in accordance with structure III.

7. The composition of claims 1 or 3 in which the organo-sulfur containing complex is in accordance with structure IV.

* * * * *

UNITED STATES PATENT AND TRADEMARK OFFICE
CERTIFICATE OF CORRECTION

PATENT NO. : 4,225,448

DATED : September 30, 1980

INVENTOR(S) : MILTON BRAID

It is certified that error appears in the above-identified patent and that said Letters Patent are hereby corrected as shown below:

Column 1, line 18, "in" should be --In--;

Column 5, line 43, "properties" should be --proportion--.

Signed and Sealed this

Third Day of February 1981

[SEAL]

Attest:

RENE D. TEGTMEYER

Attesting Officer

Acting Commissioner of Patents and Trademarks